United States Patent [19]
Regnier et al.

[11] 3,944,551
[45] Mar. 16, 1976

[54] N-COUMARANYL AND CHROMANYL -METHYL-OR SULFUR ANALOGS THEREOF-N'- THIAZOLYL PIPERAZINES

[75] Inventors: Gilbert Regnier, Chatenay-Malabry; Roger Canevari, Villebon-sur-Yvette; Michel Laubie, Vaucresson; Jean-Claude Poignantw, Bures-sur-Yvette, all of France

[73] Assignee: Science-Union et Cie, Neuilly-sur-Seine, France

[22] Filed: Mar. 25, 1974

[21] Appl. No.: 454,665

[30] Foreign Application Priority Data
Apr. 2, 1973 United Kingdom............... 15692/73

[52] U.S. Cl................... 260/268 BC; 260/256.4 N; 260/256.5 R; 260/268 BQ; 424/250
[51] Int. Cl.²....................................... C07D 295/12
[58] Field of Search............................... 260/268 BC

[56] References Cited
UNITED STATES PATENTS
3,808,212   4/1974   Renth et al................. 260/268 BC OTHER PUBLICATIONS
Petigara et al., Chemical Abstracts, Vol. 68, p. 87274t, (1968).
Peitgara et al., Chemical Abstracts, Vol. 71, p. 101818u, (1969).

*Primary Examiner*—Donald G. Daus
*Assistant Examiner*—Jose Tovar
*Attorney, Agent, or Firm*—Gordon W. Hueschen

[57] ABSTRACT

Disubstituted piperazines of the formula:

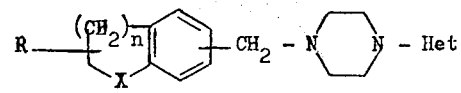

wherein:
$n$ is 1 or 2;
X is oxygen or sulfur;
R is hydrogen or lower alkyl;
Het is pyridyl, pyrimidinyl, pyridazinyl, pyrazinyl, quinolyl, quinazolyl, thiazolyl or benzothiazolyl, each optionally substituted by one or more lower alkyl, lower alkoxy, phenyl, amino, mono or di-lower-alkylamino, or hydroxy, and,

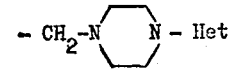

is always bonded to the benzene ring.

These compounds are used as medicines especially in the treatment of peripheral vascular disorders, Parkinson's disease, hypertension and as antipregnancy drugs.

9 Claims, No Drawings

N-COUMARANYL AND CHROMANYL -METHYL-OR SULFUR ANALOGS THEREOF-N'-THIAZOLYL PIPERAZINES

The present invention provides disubstituted piperazines of the general formula I:

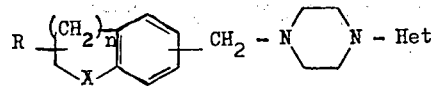   I and acid addition salts, especially physiologically tolerable acid addition salts thereof, wherein:

$n$ is an integer selected from 1 and 2;

X is selected from the group consisting of an oxygen atom and a sulfur atom;

R is selected from the group consisting of a hydrogen atom and an alkyl radical having from 1 to 3 carbon atoms inclusive;

Het is a heterocyclic radical having one or two nitrogen atoms and optionally one sulfur atom selected from the group consisting of pyridyl, pyrimidinyl, pyridazinyl, pyrazinyl, quinolyl, quinazolinyl, thiazolyl, benzothiazolyl, and each of these radicals substituted by one or more substituents selected from the group consisting of alkyl and alkoxy radicals, each having from 1 to 5 carbon atoms inclusive, phenyl, amino, mono and di-alkylamino wherein the alkyl moieties have from 1 to 5 carbon atoms inclusive and hydroxy radicals, and,

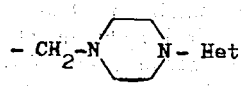

is always bonded to the benzene ring.

Due to their pharmacological properties, the preferred compounds are the compounds of the general formula I wherein $n$, X and R are as defined above and Het is selected from the group consisting of thiazolyl and benzothiazolyl radicals both optionally substituted by one or more substituents selected from the group consisting of alkyl and alkoxy radicals each having from 1 to 5 carbon atoms inclusive, phenyl amino, mono- and di-alkylamino radicals wherein the alkyl moieties have from 1 to 5 carbon atoms inclusive, and hydroxy radicals, and physiologically tolerable acid addition salts thereof.

Among these preferred compounds, the most interesting compounds are those having the general formula I wherein $n$, X and R are as defined above and Het is selected from the group consisting of thiazolyl, ($C_1$–$C_5$) alkyl thiazolyl, ($C_1$–$C_5$) alkoxy thiazolyl, phenylthiazolyl, amino thiazolyl, mono- and di-($C_1$–$C_5$) alkylamino thiazolyl and hydroxythiazolyl radicals, and physiologically tolerable acid addition salts thereof.

The compounds of the general formula I are new and they were prepared according to the following processes which are all included in the present invention.

The present invention provides a process for preparing a compound of the general formula I which comprises:

condensing a halo compound of the general formula II:

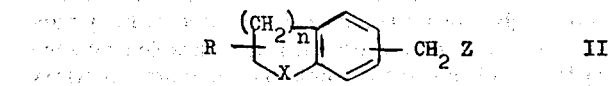   II wherein $n$, X and R have the meanings given above and Z represents a chlorine or bromine atom, and —$CH_2$Z is always bonded to the benzene ring, with a N-mono substituted piperazine of the general formula III:

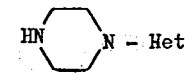   III wherein Het has the meaning given above; or condensing a halo compound of the general formula IV:

   IV wherein Het and Z have the meanings given above, with a N-monosubstituted piperazine of the general formula V:

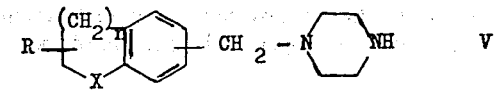   V wherein $n$, X and R have the meanings given above and

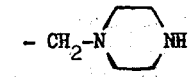

is always bonded to the benzene ring.

The above processes are advantageously carried out in solution in a polar solvent, for example an alcohol having a high boiling point, for example, butanol or pentanol or, preferably, an aliphatic amide, for example dimethylformamide or dimethylacetamide, or in a non-polar solvent for example in aromatic hydrocarbon, for example toluene or xylene. It is advantageous to carry out the processes at a temperature in the range of from 100° to 140°C in the presence of an acceptor for the hydrogen halide formed in the course of the reaction. As acceptors there may be mentioned, for example, alkali metal or alkaline-earth metal salts of carbonic acid, for example sodium or potassium bicarbonate or carbonate or calcium carbonate and organic bases, for example dimethylamine, pyridine or triethylamine; if desired there may be used instead an excess of the mono-substituted piperazine of the formula III or V, the excess acting as an acceptor.

It is moreover, advantageous, for preparing compounds of the general formula I wherein Het is substituted by one or more hydroxy radicals, to use a compound of the formula III or IV, wherein Het is correspondingly substituted, instead of by free hydroxy radicals, by one or more easily hydrogenolizable protected hydroxy radicals, for example one or more benzyloxy radicals. The product of the condensation is thereafter subjected to hydrogenolysis, by a method known for liberating hydroxy groups from protected hydroxy groups, for example in the presence of a catalyst, for example palladium on charcoal.

The present invention also provides a process for preparing a compound of the general formula I which comprises submitting a mixture of an aldehyde of the general formula VI:

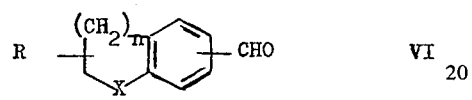   VI wherein $n$, X and R have the meanings given above, and —CHO is always bonded to the benzene ring and a N-monosubstituted piperazine of the general formula III given above, to an alkylating reduction using hydrogen at a pressure $\leq 5$ atmospheres, in the presence of a small quantity of palladium on charcoal, in a slightly polar aprotic solvent, for example, ethyl acetate or toluene; the use of a hydrogen pressure $\leq 5$ atmospheres allows an efficient control of the quantity of hydrogen which is absorbed in order to minimize the concomitant hydrogenolysis reaction of the

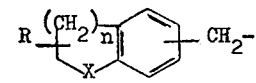

group which is formed.

Such a process is advantageously carried out by submitting to hydrogenation under a hydrogen pressure $\leq 5$ atmospheres, a substantially equimolar mixture of the compounds of the formulae III and VI, in solution in ethyl acetate, in the presence of a quantity of palladium on charcoal such that the weight of palladium is from 0.15 to 0.2 % of the total weight of the reactants of the formulae III and VI at a temperature within the range of from 50° to 80° C.

The present invention also provides a process for preparing a compound of the general formula I which comprises condensing an acyl chloride of the general formula VII:

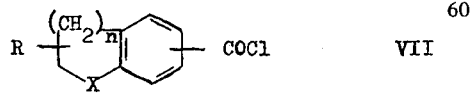   VII wherein $n$, X and R have the meanings given above and -COCl is always bonded to the benzene ring, with a piperazine of the general formula III given above, then reducing the so-obtained amide of the general formula VIII:

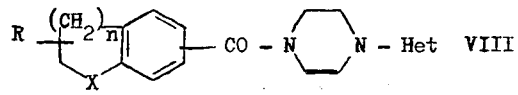   VIII wherein $n$, X, R and Het have the meanings given above and

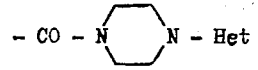

is always bonded to the benzene ring.

One of the most satisfactory way to carry out such a process consists in condensing the compounds III and VII in a solvent for example in an aromatic hydrocarbon having a low boiling point such, for example, as benzene or toluene or in an aliphatic or cycloaliphatic ether such as tetrahydrofuran or dioxane, at a temperature within the range of from 60° to 120° C, in the presence of an acceptor for the hydrochloric acid formed during the reaction. As acceptors there may be used an excess of the piperazine III or a tertiary amine such for example, as triethylamine, pyridine, or dimethylaniline.

A particularly suitable method for reducing the amide VIII consists in using lithium aluminium hydride, the reduction being performed in a solvent having a low boiling point such for example, as ether or tetrahydrofuran, at a temperature within the range of from 35° to 60° C.

The present invention also provides a process for preparing a compound of the general formula I which comprises condensing a chloro compound of the general formula IX:

   IX wherein Het has the meaning given above,
with an amine of the general formula X:

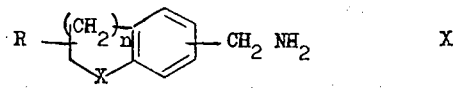   X wherein $n$, X and R have the meanings given above and — $CH_2 NH_2$ is always bonded to the benzene ring.

Such a condensation is advantageously carried out in a suitable solvent, at a temperature within the range of from 130° to 150° C, in the presence of an acceptor for the hydrochloric acid, so formed during the reaction. As solvents which may be used in such a case there may be especially mentioned the alcohols having 5 or 6 carbon atoms such for example, as isoamyl alcohol, glycol ethers such, for example, as diglyme, and tertiary amides such, for example, as dimethylformamide and dimethyl acetamide. As an acceptor, there may be used, advantageously an excess of the amine X, or if desired, a tertiary amine such, for example, as pyridine or dimethylaniline.

The chloro compounds of the general formula IX were prepared by chlorinating the corresponding hydroxy compounds of the general formula:

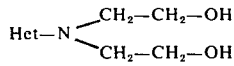

wherein Het has the meanings given above.

The compounds of the general formula I are weak bases which may be converted by treatment with acids into acid addition salts. As acids which may be used for the formation of these addition salts there may be mentioned, for example, in the mineral series: hydrochloric, hydrobromic, sulfuric and phosphoric acids, and in the organic series: acetic, propionic, maleic, fumaric, tartaric, citric, oxalic, benzoic, methanesulphonic and isethionic acids.

The compounds of the formula I may be purified by physical methods, for example by distillation, crystallization or chromatography, or by chemical methods, for example by formation of an addition salt followed by crystallization of the latter and decomposition thereof with an alkaline agent.

The compounds of the general formula I and physiologically tolerable salts thereof possess valuable pharmacological and therapeutic properties especially peripheral vasodilator, anti-Parkinson, antihypertensive and antipregnancy properties. They may, therefore, be used as medicines especially in the treatment of peripheral vascular disorders, Parkinson's disease, hypertension and in the prevention of pregnancy.

Their toxicity is low and their $LD_{50}$ determined in mice varies from 100 to 715 mg/kg by intraperitoneal route.

Their neuroleptic properties were evidenced in the rat and mice by modifications observed on the stereotypy, motility and excitation.

In mice, the average efficace dose is about 100 mg/kg by intraperitoneal route. At this dose, there were observed a decrease of motility and tonus.

The scores of CNS stimulation or stereotypy were determined according to the method of Quinton and Haliwell, Nature 200, 178 (1963). Scores of up to 266 for 3 hours, and up to 419 for 5 hours and a half, were observed with doses of 20 to 80 mg/kg I.P.

The present invention also provides pharmaceutical compositions which contains a compound of the general formula I or a physiologically tolerable salt thereof in admixture or conjunction with a pharmaceutically suitable carrier, such for example, as distilled water, glucose, lactose, starch, talc, magnesium stearate, ethyl cellulose or cocoa butter.

The so-obtained pharmaceutical compositions are advantageously in unit dosage form and may contain from 15 to 300 mg of the active ingredient.

These pharmaceutical compositions may be in form of tablets, dragees, capsules, suppositories or injectable or drinkable solutions and may be administered by oral, rectal or parenteral route at a dose of 15 to 300 mg, 1 to 5 times a day.

The following examples illustrate the invention, the melting points being determined on a Kofler block (K) or in a capillary tube (cap.).

EXAMPLE 1

1-(5-coumaranyl methyl)-4-(2-pyrimidinyl) piperazine

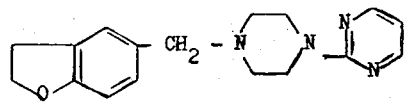

First method:

A mixture of 16.9 g (0.1 mole) of 5-chloromethyl coumaran, M.P. (K) 41°–42°C and 32 g (0.2 mole) of 1-(2-pyrimidinyl) piperazine in 150 ml of anhydrous toluene was heated for 9 hours at boiling point. The salt (1-(2 pyrimidinyl)-piperazine hydrochloride) which had separated out was filtered off and then the filtrate was extracted several times with normal methanesulfonic acid. The acidic medium was washed with ether and was then rendered alkaline with an excess of potassium carbonate. The so-obtained base was extracted with chloroform and the chloroform solution was washed several times with water, was dried on potassium carbonate and was then evaporated under reduced pressure. There were obtained 25 g of residue which was recrystallized from 70 ml of ethanol. There were obtained 19 g of white cyrstals of 1-(5-coumaranyl methyl)-4-(2-pyrimidinyl) piperazine, melting (K) at 102° C.

Second method:

A solution of 11.5 g of 2-chloropyrimidine and 22g of 1-(5-coumaranyl methyl) piperazine in 150 ml of dimethylformamide in the presence of 28 g of dried potassium carbonate was heated for 9 hours at boiling point. The salt which had separated out was filtered off the solvent was evaporated under a reduced pressure and the so-obtained semicrystalline residue was dissolved in 75 ml of boiling ethanol. After cooling, the product was suction-filtered off. There were obtained 18 g of white crystals of 1-(5-coumaranyl methyl)-4-(2-pyrimidinyl) piperazine, melting (K) at 102° C.

Third method:

A solution of 7.5 g of 5-formyl coumaran, B.P./13 mmHg = 143°-145°C, $n_D^{22}$ = 1.597, and 7.5 g of 1-(2-pyrimidinyl)-piperazine in 400 ml of ethyl acetate was hydrogenated for 1 ½ hours under a pressure of hydrogen ≤ 5 atmospheres in the presence of 4 g of palladised charcoal (5 % Pd). The temperature was maintained at 80°C throughout hydrogenation. After hydrogenation, the catalyst was filtered off and the filtrate was extracted several times with normal methanesulfonic acid. The acid solution was washed with ether and was then rendered alkaline with an excess of potassium carbonate. The so-obtained base was extracted several times with ether. The etheral extracts were mixed together and were then dried over potassium carbonate. The ether was evaporated off and the residue (8g) was recrystallized from 20 ml of ethanol. There were obtained 5 g of white crystals of 1-(5-coumaranyl methyl)-4-(2-pyrimidinyl) piperazine, melting (K) at 102° C.

Fourth method:

To a solution of 8.2 g of 1-(2-pyrimidinyl)-piperazine and 5g of anhydrous triethylamine in 200 ml of anhydrous tetrahydrofuran, there were added dropwise a solution of 9.1 g of 5-coumaranyl carboxylic acid chloride in 20 ml of tetrahydrofuran. After the completion of the addition, the reaction mixture was heated at 60° C for 2 hours, then the so-formed precipitate was suction-filtered off. The filtrate was evaporated under reduced pressure and the crystalline residue was washed with water then recrystallized in 70 ml of ethanol. There were obtained 12 g of 1-(5-coumaranyl carbonyl)-4-(2-pyrimidinyl) piperazine, melting (K) at 149°–150° C.

A solution of 12 g of 1-(5-coumaranyl carbonyl)-4-(2-pyrimidinyl) piperazine and 125 ml of anhydrous tetrahydrofuran was heated, at the boiling temperature, in the presence of 1.4 g of lithium aluminium hydride, for 18 hours. Then the mixture was cooled and there were successively added 2 ml of water, 2 ml of a 2 N sodium hydroxide solution and 6 ml of water. The so-formed precipitate of alumina was filtered off and the solvent was evaporated under a reduced pressure. The crystallized residue was treated with 50 ml of normal hydrochloric acid. The unsoluble matter was filtered off; the filtrate was rendered alkaline with an excess of potassium carbonate then extracted with ether. After evaporation of ether the crystalline residue was taken up with boiling ethanol. There were finally obtained after crystallization, 10.2 g of white crystals of 1-(5-coumaranyl methyl)-4-(2-pyrimidinyl) piperazine, melting (K) at 102° C.

Fifth method:

A mixture of 22 g of 2-[bis-(β-chloroethyl) amino] pyrimidine, 44.7 g of 5-aminomethyl coumaran and 300 ml of diglyme was heated at 150° C for 12 hours. Then, the solvent was eliminated under a reduced pressure and the viscous residue was taken up with 300 ml of water and 300 ml of benzene.

After decantation, the aqueous phase was extracted with benzene. The organic phase was then extracted several times with a normal solution of methane sulfonic acid and the acid portion was then rendered alkaline with an excess of potassium carbonate. The so-obtained oily base was extracted with ether. The etheral layer was dried, then ether was evaporated and the syrupy residue was dissolved in 500 ml of boiling ethanol. There were obtained after crystallization 12 g of white crystals of 1-(5-coumaranyl methyl)-4-(2-pyrimidinyl) piperazine, melting (K) at 102° C.

EXAMPLE 2

1-(5-coumaranyl methyl)-4-(2-thiazolyl) piperazine

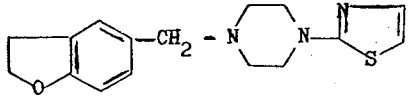

First method:

A mixture of 16.9 g (0.1 mole) of 5-chloromethyl coumaran and 33.8 g (0.2 mole) of 1-(2-thiazolyl) piperazine in 500 ml of anhydrous toluene and 10 ml of dimethylformamide was heated at 100° C for 6 hours. The salt, 1-(2-thiazolyl) piperazine hydrochloride, which had separated out was filtered off and then the filtrate was extracted several times with normal methanesulfonic acid. The acidic medium was washed with ether and was then rendered alkaline with an excess of potassium carbonate. The so-obtained base was extracted with chloroform and the chloroform solution was washed several times with water, was dried on potassium carbonate and was then evaporated under reduced pressure. There were obtained a residue which was recrystallized from ethanol. There were obtained 11 g of white crystals of 1-(5-coumaranyl methyl)-4-(2thiazolyl) piperazine, melting (K) at 95° C.

Second method:

A solution of 12 g of 2-chlorothiazole and 22 g of 1-(5-coumaranyl methyl) piperazine in 150 ml of dimethylformamide in the presence of 28 g of dried potassium carbonate was heated for 9 hours at boiling point. The salt which had separated out was filtered off the solvent was evaporated under a reduced pressure and the so-obtained semicrystalline residue was dissolved in 75 ml of boiling ethanol. After cooling, the product was suction-filtered off. There were obtained 18.5 g of white crystals of 1-(5-coumaranyl methyl)-4-(2-thiazolyl) piperazine, melting at 95° C (K).

Third method:

A solution of 7.4 g of 5-formyl coumaran B.P./13 mmHg = 143°–145° C, $n_D^{22}$ = 1.597, and 7.6 g of 1-(2-thiazolyl) piperazine in 400 ml of ethyl acetate was hydrogenated for 1 ½ hours under a pressure of hydrogen ≤ 5 atmospheres in the presence of 4 g of palladised charcoal (5 % Pd). The temperature was maintained at 80° C throughout hydrogenation. After hydrogenation, the catalyst was filtered off and the filtrate was extracted several times with normal methanesulfonic acid. The acid solution was washed with ether and was then rendered alkaline with an excess of potassium carbonate. The so-obtained base was extracted several times with ether. The etheral extracts were mixed together and were then dried over potassium carbonate. The ether was evaporated off and the residue was recrystallized from 20 ml of ethanol. There were obtained 5 g of white crystals of 1-(5-coumaranyl methyl)-4-(2-thiazolyl) piperazine, melting (K) at 95° C.

Fourth method:

To a solution of 9 g of 1-(2-thiazolyl) piperazine and 5 g of anhydrous triethylamine in 200 ml of anhydrous tetrahydroduran, there were added dropwise, a solution of 9.1 g of 5-coumaranyl carboxylic acid chloride in 20 ml of tetrahydrofuran. After the completion of the addition, the reaction mixture was heated at 60° C for two hours, then, the so-formed precipitate was suction-filtered off. The filtrate was evaporated under reduced pressure and the crystalline residue was washed with water then recrystallized in 70 ml of ethanol. There were obtained 12 g of 1-(5-coumaranyl carbonyl)-4-(2-thiazolyl) piperazine, melting (K) at 150°–151° C.

A solution of 10 g of 1-(5-coumaranyl carbonyl)-4-(2-thiazolyl) piperazine and 125 ml of anhydrous tetrahydrofuran was heated at the boiling temperature, with 1.4 g of lithium aluminium hydride, for 18 hours. Then, the mixture was cooled and there were successively added 2 ml of water, 2 ml of a 2 N sodium hydroxide solution and 6 ml of water. The so-formed precipitate of alumina was filtered off and the solvent was evaporated under a reduced pressure. The crystallized residue was heated with 50 ml of normal hydrochloric acid. The unsoluble matter was filtered off; the filtrate was rendered alkaline with an excess of potassium carbonate then extracted with ether. After evaporation of ether the crystalline residue was taken up with boiling ethanol. There were finally obtained after crystallization, 7.3 g of white crystals of 1-(5-coumaranyl methyl)-4-(2-thiazolyl) piperazine, melting (K) at 95°C.

Fifth method:

A mixture of 11.2 g of 2-[bis-(β-chloroethyl)amino] thiazole, 22.4 g of 5-aminomethyl coumaran and 300 ml of diglyme was heated at 150°C for 12 hours. Then, the solvent was eliminated under a reduced pressure and the viscous residue was taken up with 300 ml of water and 300 ml of benzene. After decantation, the aqueous phase was extracted with benzene. The organic phase was then extracted several times with a normal solution of methane sulfonic acid and the acid portion was then rendered alkaline with an excess of potassium carbonate. The so-obtained oily base was extracted with ether. The etheral layer was dried, then ether was evaporated and the syrupy residue was dissolved in 500 ml of boiling ethanol. There were obtained after crystallization 7.1 g of white crystals of 1-(5-coumaranyl methyl)-4-(2-thiazolyl) piperazine melting (K) at 95° C.

EXEMPLE 3 to 36

The compounds of the general formula I, the substituents and the melting point of which are mentioned in the following table, page 10, were prepared according to the processes describes in Examples 1 and 2.

| No. Ex | n | X | R | Position of —CH$_2$—N⟨ ⟩N—Het * on the benzene ring | Het | Melting Point |
|---|---|---|---|---|---|---|
| 1 | 1 | 0 | H | β |  | 102° C (K) |
| 2 | 1 | 0 | H | β |  | 95° C (K) |
| 3 | 1 | 0 | H | β |  | 115–117° C(cap) |
| 4 | 1 | 0 | (2)CH$_3$ | β |  | 78–79°C(cap) |
| 5 | 1 | 0 | (2)CH$_3$ | β |  | 100–101°C(cap) |
| 6 | 1 | 0 | (2)CH$_3$ | β |  | 68–69°C(cap) |
| 7 | 1 | 0 | H | β |  | 2 NCl ½ H$_2$O 226–229°C (cap) |
| 8 | 1 | 0 | (2)CH$_3$ | β |  | HCl 229–230°C(cap) |
| 9 | 1 | 0 | (2)CH$_3$ | β |  | 156–158°C(cap) |
| 10 | 1 | 0 | (2)CH$_3$ | β |  | 2 HCl 243–245°C(cap) |
| 11 | 1 | 0 | (2)CH$_3$ | β |  | 2 HCl 220–225°C(cap) |
| 12 | 1 | 0 | (2)CH$_3$ | β |  | 188–191°C |

-continued
| No. Ex | n | X | R | Position of —CH$_2$—N⟨ ⟩N—Het * on the benzene ring | Het | Melting Point |
|---|---|---|---|---|---|---|
| 13 | 1 | 0 | $_{(2)}$CH$_3$ | β | 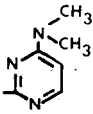 | 104–106°C(cap) |
| 14 | 1 | 0 | $_{(2)}$CH$_3$ | β | 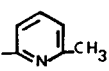 | 2 HCl 196–198°C(cap) |
| 15 | 1 | 0 | $_{(2)}$CH$_3$ | β | 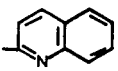 | 2 HCl 275–277°C(cap) |
| 16 | 1 | 0 | H | β | 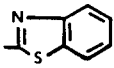 | 161–163°C(cap) |
| 17 | 1 | 0 | H | β | 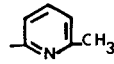 | 2 HCl 215–220°C(cap) |
| 18 | 1 | 0 | H | β | 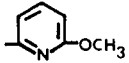 | 2 HCl 220–225°C(cap) |
| 19 | 1 | 0 | H | β | 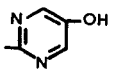 | 2 HCl 280–285°C(cap) |
| 20 | 1 | 0 | (2)CH$_3$ | β |  | 170–172°C(cap) |
| 21 | 1 | 0 | $_{(2)}$CH$_3$ | β | 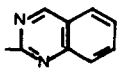 | 2 HCl 256–258°C(cap) |
| 22 | 1 | 0 | $_{(2)}$CH$_3$ | β |  | 2 HCl 215–220°C(cap) |
| 23 | 1 | 0 | $_{(2)}$CH$_3$ | β |  | 157–158°C(cap) |
| 24 | 1 | 0 | H | γ |  | 105–106°C(cap) |
| 25 | 2 | 0 | H | β |  | 98–100°C(cap) |

| No. Ex | n | X | R | Position of —CH₂—N⌒N—Het* on the benzene ring | Het | Melting Point |
|---|---|---|---|---|---|---|
| 26 | 2 | O | H | β | pyrimidinyl | 2 HCl 192–196°C |
| 27 | 2 | O | H | β | thiazolyl | 103–106°C |
| 28 | 1 | S | H | β | pyrimidinyl | 127–128°C(cap) |
| 29 | 1 | S | H | β | pyridyl | 142–143°C(cap) |
| 30 | 1 | S | H | β | thiazolyl | 120–121°C(cap) |
| 31 | 2 | S | H | β | pyrimidinyl | HCl 250–253°C(cap) |
| 32 | 2 | S | H | β | pyridyl | HCl, H₂O 224–227°C(cap) |
| 33 | 2 | S | H | β | thiazolyl | 133–136°C(cap) |
| 34 | 2 | S | H | δ | pyrimidinyl | 2 HCl 234–238°C(cap) |
| 35 | 2 | S | H | δ | pyridyl | 84–86°C (cap) |
| 36 | 2 | S | H | δ | thiazolyl | 80–82°C (cap) |

* $_{(2)}CH_3$ shows that the methyl group is bonded on the heterocyclic ring in 2- position.

The starting materials used for preparing the compounds of Examples 3 to 36 were:
as regards to the halo compounds of formula II used in the first preparative method:
5-chloromethyl coumaran in examples 3, 7 and 16 to 19;
2methyl-5-chloromethyl coumaran in examples 4 to 6, 8 to 15 and 20 to 23;
6-chloromethyl coumaran in example 24;
6-chloromethyl chroman in examples 25 to 27;
5-chloromethyl thiocoumaran in examples 28 to 30;
6-chloromethyl thiochroman in examples 31 to 33; and
8-chloromethyl thiochroman in examples 34 to 36.

as regards to the piperazines of formula III used in the first, third and fourth preparative methods:
1(2-pyridyl) piperazine in examples 3,6,25,29,32 and 35;
1-(2-pyrimidinyl) piperazine in examples 4,26,28,31, and 34;
1-(2-thiazolyl) piperazine, in examples 5,24,27,30,33 and 36;

1-(4-methyl-2-thiazolyl) piperazine, in example 7;
1-(6-methoxy-2-pyridyl) piperazine in examples 8 and 19;
1-(2-benzothiazolyl) piperazine, in examples 9 and 16;
1-(6-pyridazinyl) piperazine, in example 10;
1-(2-pyrazinyl) piperazine, in example 11;
1-(4-hydroxy-2-pyrimidinyl) piperazine in example 12;
1(5-hydroxy-2-pyrimidinyl) piperazine in examples 19 and 23;
1-(4-dimethylamino-2-pyrimidinyl) piperazine in example 13;
1-(4-amino-2-pyrimidinyl) piperazine in example 20;
1-(4-methoxy-2-pyrimidinyl) piperazine in example 22;
1-(6-methyl-2-pyridyl) piperazine, in examples 14 and 17;
1-(2-quinazolinyl) piperazine, in examples 15 and 21;

as regards to the halo compounds of formula IV used in the second preparative method:
2-chloropyridine in examples 3,6,25,29,32 and 35;
2-chloropyrimidine in examples 4,26,28,31 and 34;
2-chlorothiazole in examples 5,24,27,30,33 and 36;
2-chloro-4-methyl thiazole in example 7;
2-chloro-6-methoxy pyridine, in examples 8 and 19;
2-chlorobenzothiazole in examples 9 and 16;
6-chloro pyridazine in example 10;
2-chloropyrazine in example 11;
2-chloro-4-hydroxy pyrimidine, in example 12;
2-chloro-5-hydroxy pyrimidine in examples 19 and 23;
2chloro-4-dimethylamino pyrimidine in example 13;
2-chloro-4-amino pyrimidine in example 20;
2-chloro-4-methoxy pyrimidine, in example 22;
2-chloro-6-methyl pyridine in examples 14 and 17;
2-chloroquinazoline in examples 15 and 21.

as regards to the N-monosubstituted piperazines of formula V used in the second preparative method:
1-(5-coumaranyl methyl)piperazine in examples 3,7 and 16;
1-(2-methyl-5-coumaranyl methyl) piperazine in examples 4 to 6, 8 to 15 and 20 to 23;
1-(6-coumaranyl methyl) piperazine in example 24;
1-(6-chromanyl methyl) piperazine in examples 25 to 27;
1-(5-thiocoumaranyl methyl) piperazine, in examples 28 to 30;
1(6-thiochromanyl methyl) piperazine in examples 31 to 33; and
1-(8-thiochromanyl methyl) piperazine in examples 34 to 36.

as regards to the aldehydes of formula VI used in the third preparative method:
5-formyl coumaran in examples 3,7 and 16 to 19;
2-methyl-5-formyl coumaran in example 4 to 6, 8 to 15 and 20 to 23;
6-formyl coumaran in example 24;
6-formyl chroman in example 25 to 27;
5-formyl thiocoumaran in example 28 to 30;
6-formyl thiochroman in examples 31 to 33; and
8-formyl thiochroman in examples 34 to 36.

as regards to the acyle chloride of formula VII used in the fourth preparative method:
5-coumaranyl carboxylic acid chloride in examples 3,7 and 16 to 19;
2-methyl-5-coumaranyl carboxylic acid chloride in examples 4 to 6, 8 to 15 and 20 to 23;
6-coumaranyl carboxylic acid chloride in example 24;
6-chromanyl carboxylic acid chloride in examples 25 to 27;
5-thiocoumaranyl carboxylic acid chloride in examples 28 to 30;
6-thiochromanyl carboxylic acid chloride in examples 31 to 33;
8-thiochromanyl carboxylic acid chloride in examples 34 to 36.

as regards to chloro compounds of formula IX used in the fifth preparative method:
2-[bis-($\beta$-chloroethyl) amino] pyridine in examples 3,6,25,29,32 and 35;
2-[bis-($\beta$-chloroethyl) amino] pyrimidine in examples 4,26,28,31 and 34;
2-[bis-($\beta$chloroethyl) amino] thiazole in examples 5,24,27,30,33 and 36;
2-[bis-($\beta$-chloroethyl) amino]-4-methyl thiazole in example 7;
2-[bis-($\beta$-chloroethyl) amino]-6-methoxy pyridine in examples 8 and 19;
2-[bis-($\beta$-chloroethyl) amino] benzothiazole in examples 9 and 16;
6-[bis-($\beta$-chloroethyl) amino] pyridazine in example 10;
2-[bis-($\beta$-chloroethyl) amino]pyrazine in example 11;
2-[bis-($\beta$-chloroethyl) amino]-4-hydroxy pyrimidine in example 12;
2-[bis-($\beta$-chloroethyl) amino]-5-hydroxy pyrimidine in examples 19 and 23;
2-[bis-($\beta$-chloroethyl)amino]-4-dimethylamino pyrimdine, in example 13;
2-[bis-($\beta$-chloroethyl) amino]-4-amino pyrimidine in example 20;
2-[bis-($\beta$-chloroethyl) amino]-4-methoxy pyrimidine in example 22;
2-[bis-($\beta$-chloroethyl) amino]-6-methyl pyridine in examples 14 and 17; and
2-[bis-($\beta$-chloroethyl) amino] quinazoline in examples 15 and 21.

as regards to the amines of formula X used in the fifth preparative method:
5-aminomethyl coumaran in examples 3, 7 and 16 to 19;
2-methyl-5-aminomethyl coumaran in examples 4 to 6, 8 to 15 and 20 to 23;
6-aminomethyl coumaran in example 24;
6-aminomethyl chroman in examples 25 to 27;
5-aminomethyl thiocoumaran in examples 28 to 30;
6-aminomethyl thiochroman in examples 31 to 33; and
8-aminomethyl thiochroman in examples 34 to 36.

We claim:
1. A compound selected from the group consisting of:
A. disubstituted piperazines of the formula I:

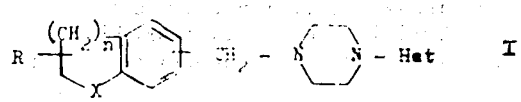

wherein:
  $n$ is selected from 1 and 2;
  X is selected from the group consisting of oxygen and sulfur;
  R is selected from the group consisting of hydrogen and alkyl having from 1 to 3 carbon atoms inclusive;
  Het is selected from the group consisting of thiazolyl, methyl thiazolyl benzothiazolyl, and

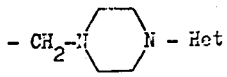

is always bonded to the benzine ring, and,

B. physiologically tolerable acid addition salts thereof.

2. A compound of claim 1 which is 1-(5-coumaranyl methyl)-4-(2-thiazolyl) piperazine.

3. A compound of claim 1 which is 1-(2-methyl 5-coumaranylmethyl)-4-(2-thiazolyl)piperazine.

4. A compound of claim 1 which is 1-(5-coumaranyl methyl)-4-(4-methyl 2-thiazolyl)piperazine.

5. A compound of claim 1 which is 1-(6-coumaranyl methyl)-4-(2-thiazolyl)piperazine.

6. A compound of claim 1 which is 1-(6-chromanyl methyl)-4-(2-thiazolyl)piperazine.

7. A compound of claim 1 which is 1-(5-thiocoumaranyl methyl)-4-(2-thiazolyl) piperazine.

8. A compound of claim 1 which is 1-(6-thiochromanyl methyl)-4-(2-thiazolyl)piperazine.

9. A compound of claim 1 which is 1-(8-thiochromanyl methyl)-4-(2-thiazolyl)piperazine.

* * * * *